United States Patent
Kawahata (10) Patent No.: US 6,862,942 B2
(45) Date of Patent: Mar. 8, 2005

(54) SURFACE PRESSURE DISTRIBUTION SENSOR

(75) Inventor: Ken Kawahata, Miyagi-ken (JP)

(73) Assignee: Alps Electric Co., Ltd., Tokyo (JP)

( * ) Notice: Subject to any disclaimer, the term of this patent is extended or adjusted under 35 U.S.C. 154(b) by 0 days.

(21) Appl. No.: 10/810,136

(22) Filed: Mar. 26, 2004

(65) Prior Publication Data
US 2004/0206190 A1 Oct. 21, 2004

(30) Foreign Application Priority Data
Apr. 18, 2003 (JP) ........................................ 2003-114085

(51) Int. Cl.$^7$ ................................................ G01D 7/00
(52) U.S. Cl. ................ 73/862.046; 73/862; 73/862.041
(58) Field of Search .............. 73/862, 862.041–862.046

(56) References Cited

U.S. PATENT DOCUMENTS

| | | | |
|---|---|---|---|
| 5,400,662 A | 3/1995 | Tamori | |
| 6,234,031 B1 * | 5/2001 | Suga | 73/862.474 |
| 6,327,376 B1 * | 12/2001 | Harkin | 382/124 |
| 6,481,294 B2 * | 11/2002 | Zellner et al. | 73/862.046 |
| 6,578,436 B1 * | 6/2003 | Ganapathi et al. | 73/862.046 |
| 6,672,174 B2 * | 1/2004 | Deconde et al. | 73/862.046 |

\* cited by examiner

Primary Examiner—Edward Lefkowitz
Assistant Examiner—Alandra Ellington
(74) Attorney, Agent, or Firm—Beyer Weaver & Thomas LLP (57) ABSTRACT

A surface pressure distribution sensor includes a row-line portion and a column-line portion that face each other with a certain spacing therebetween by a spacer. The row-line portion includes a glass substrate, multiple row lines formed on the glass substrate so as to extend in parallel to each other in a first direction, and an insulating film that covers the row lines. The column-line portion includes a flexible film and multiple column lines formed on the flexible film so as to extend in parallel to each other in a second direction orthogonal to the first direction.

7 Claims, 8 Drawing Sheets

SURFACE PRESSURE DISTRIBUTION SENSOR

BACKGROUND OF THE INVENTION

1. Field of the Invention

The present invention relates to a surface pressure distribution sensor for detecting small irregularities of an object to be sensed.

2. Description of the Related Art

A surface pressure distribution sensor for detecting small irregularities in a surface of an object brought into contact with the sensor surface, as a pressure distribution, is described in, for example, Japanese Examined Patent Application Publication No. 7-58234 (corresponding to U.S. Pat. No. 5,400,662), showing a sensor for detecting the configuration of a coarse surface as data values.

Figure 11:
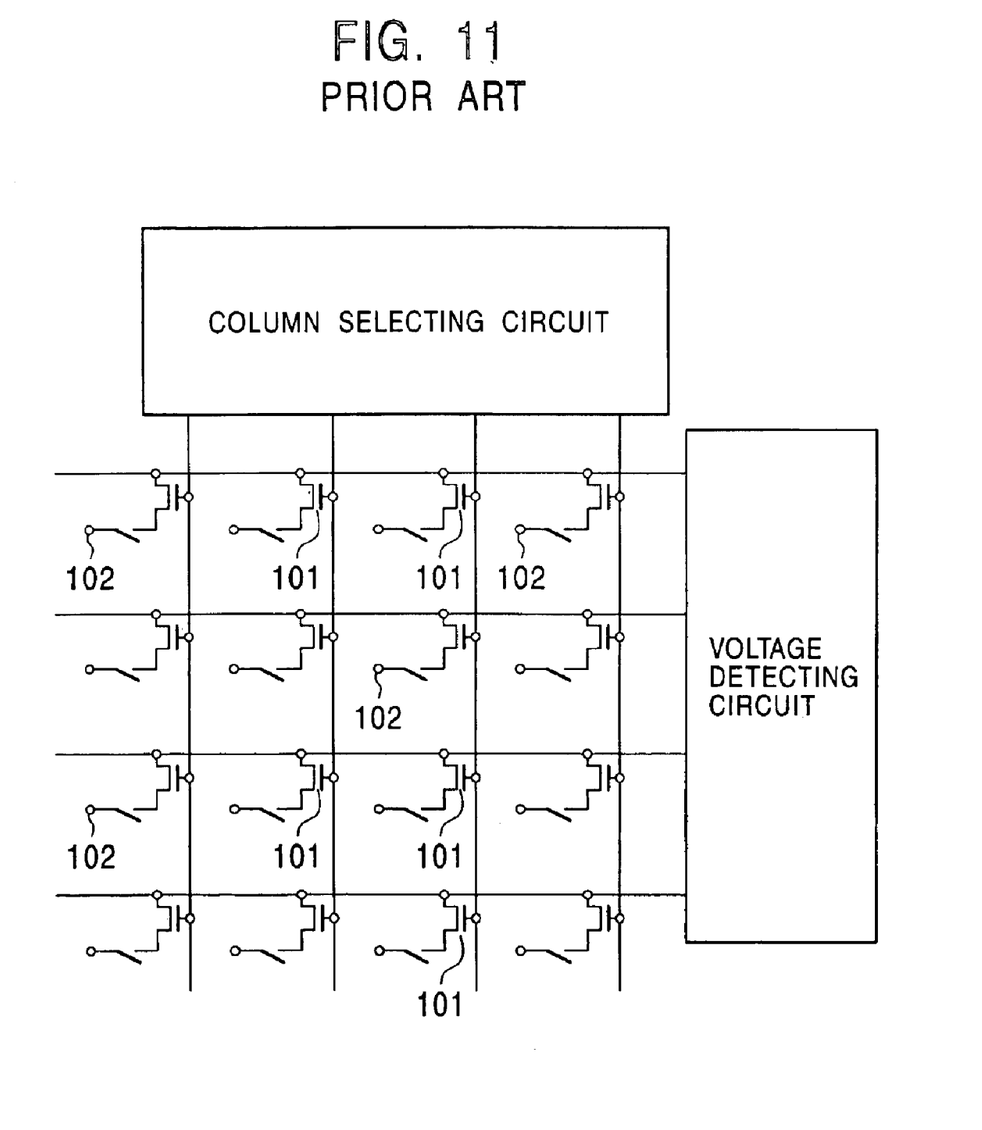
FIG. 11 is an equivalent circuit diagram of a surface pressure distribution sensor of the related art.

As shown in, for example, FIG. 11, such a surface pressure distribution sensor includes a matrix of semiconductor switching devices 101, and electrodes 102 each connected with one end of each of the semiconductor switching devices 101. A flexible film coated with a conductor is formed so as to face electrodes on the opposing side of a semiconductor substrate with a certain spacing therebetween. A voltage is applied to the conductive coating. When an object having small irregularities is pressed against the flexible film, the film is deflected along the irregularities of the object. The conductive coating of the deflected film is brought into contact with the electrodes on the semiconductor substrate, thus allowing the matrix of the corresponding semiconductor switching devices to be activated in turn for detection.

Such a surface pressure distribution sensor of the related art includes a semiconductor substrate, but semiconductor substrates are generally expensive. In particular, when the surface pressure distribution sensor is used as a fingerprint detection sensor, the expensive semiconductor substrate must have an area large enough to be contacted with the finger, thus increasing the production cost. In addition, for the purpose of detection of small irregularities, stable contact between the exposed portion of the semiconductor switching devices and the conductive coating, which is caused by even a small pressure, must be maintained for a long period of time. However, in the surface pressure distribution sensor of the related art, it is difficult to maintain the contact area between the exposed portion of the semiconductor switching devices and the conductive coating clean for a long period of time.

SUMMARY OF THE INVENTION

Accordingly, it is an object of the present invention to provide a simple and low-cost surface pressure distribution sensor capable of stable and high-precision detection of a pressure distribution for a long period of time.

In order to overcome the object described above, a surface pressure distribution sensor according to the present invention includes row lines having a plurality of conductors extending in parallel to each other in a first direction, column lines having a plurality of conductors extending in parallel to each other in a second direction across the first direction, and a substrate including the row lines and a substrate including the column lines, wherein at least one of the substrates is a flexible film substrate. A pressure distribution is detected based on an electrostatic capacitance change at intersections of the row lines and the column lines.

This surface pressure distribution sensor allows for high-precision detection of small irregularities, that is, small variations of the electrostatic capacitance. As the distance between the intersections of the row lines and the column lines varies depending upon the irregularities, the electrostatic capacitance also varies. The variations in the electrostatic capacitance are detected. The surface pressure distribution sensor can be manufactured at low cost with a simple structure.

The row lines and the column lines may be formed on first and second independent substrates, respectively, and the first and second substrates may overlap so that the row lines and the column lines intersect with each other. It is to be noted that the row lines and the column lines face each other with a spacing therebetween so that the intersections have an electrostatic capacitance.

The substrates may be formed of a single flexible film substrate. This flexible film substrate having the row lines and the column lines may be folded at a predetermined position so that the row lines and the column lines intersect with each other. Therefore, the surface pressure distribution sensor can be manufactured at lower cost with a simpler structure.

The flexible film substrate may be made of a resin having different thermal shrinkages in the first and second directions. If a tensile stress is caused by the row or column lines, the row lines and the column lines may be formed so as to extend in the higher-thermal-shrinkage direction. If a compressive stress is caused by the row or column lines, the row lines and the column lines may be formed so as to extend in the lower-thermal-shrinkage direction. This prevents disconnection of the row and column lines that can be caused by a film stress in the flexible film substrate.

Preferably, at least either the row lines or the column lines are coated with an insulating film, thus ensuring an electrostatic capacitance at the intersections of the row lines and the column lines.

The flexible film substrate may be made of a resin having different thermal shrinkages in the first and the second directions. If a tensile stress is caused by the row or column lines and the insulating film, the row lines and the column lines may be formed so as to extend in the higher-thermal-shrinkage direction. If a compressive stress is caused by the row or column lines and the insulating film, the row lines and the column lines may be formed so as to extend in the lower-thermal-shrinkage direction. This prevents disconnection of the row and column lines that can be caused by a film stress in the flexible film substrate.

The row lines and the column lines may be formed on the flexible film substrate so as to extend in the same direction, and this flexible film substrate may be folded so that the row lines and the column lines intersect with each other.

DESCRIPTION OF THE PREFERRED EMBODIMENTS

A surface pressure distribution sensor according to the present invention will be described hereinbelow.

Figure 1:
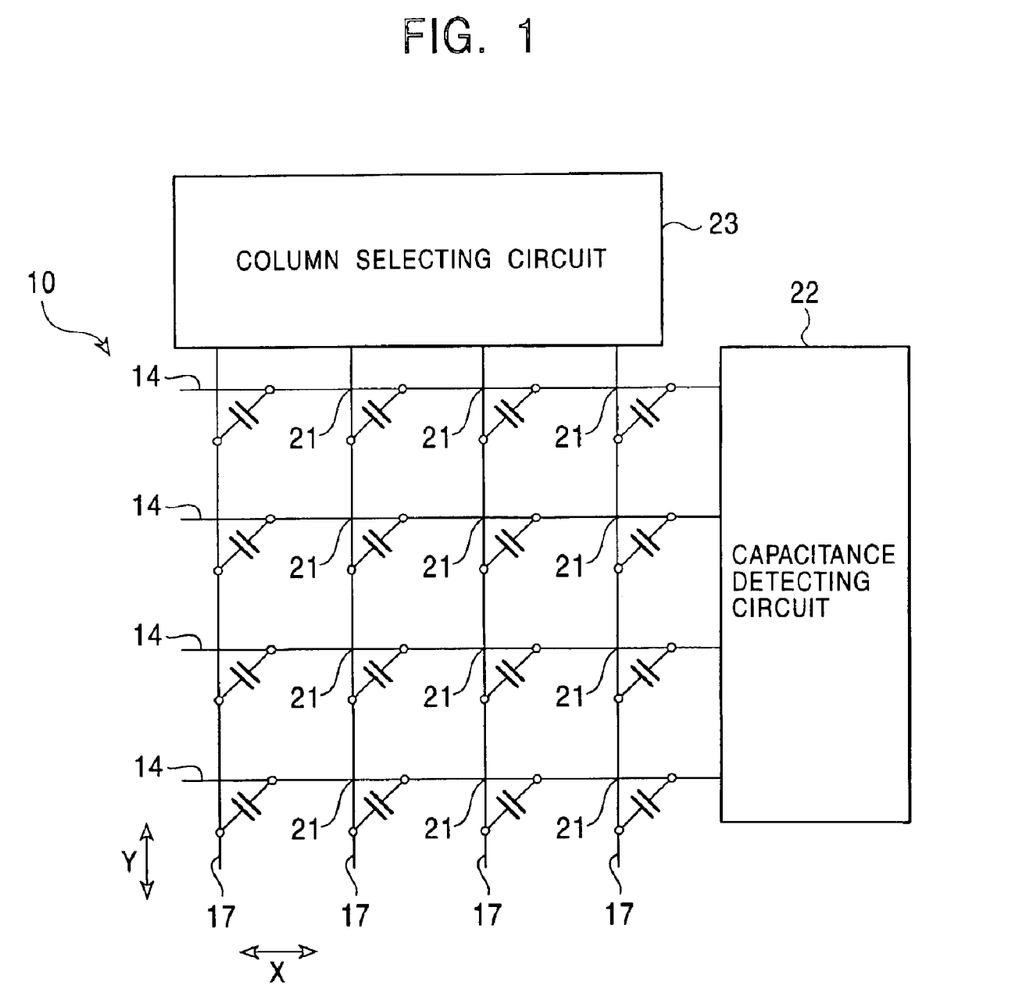
FIG. 1 is an equivalent circuit diagram of a surface pressure distribution sensor of the present invention.
Figure 2:
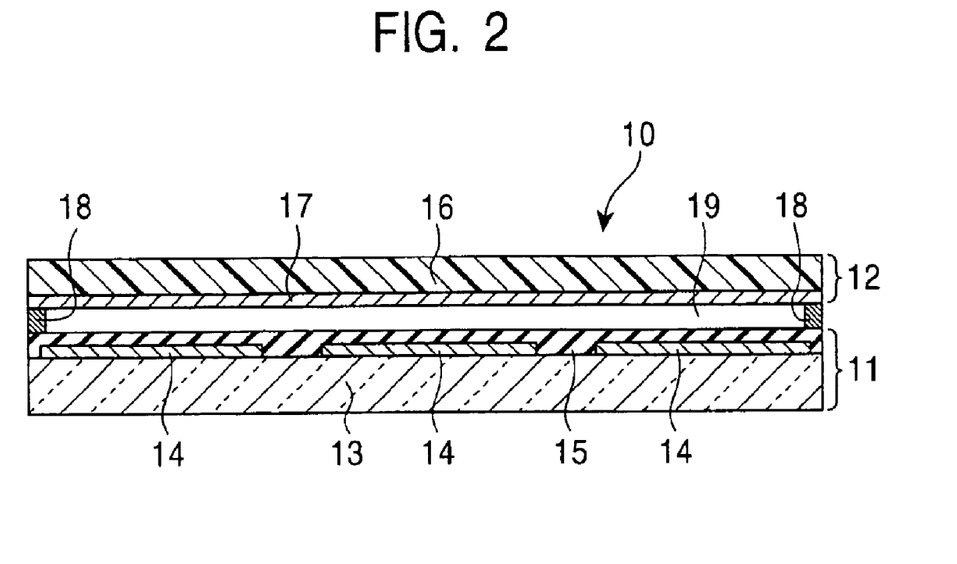
FIG. 2 is a cross-sectional view of the main portion of the surface pressure distribution sensor of the present invention in an enlarged form.

FIG. 1 is an equivalent circuit diagram of a surface pressure distribution sensor 10 according to a representative embodiment of the present invention, and FIG. 2 is a cross-sectional view of the main portion of the surface pressure distribution sensor 10 in an enlarged form. The surface pressure distribution sensor 10 includes a row-line portion 11 and a column-line portion 12 that face each other with a certain spacing therebetween by a spacer 18.

The row-line portion 11 includes a glass substrate 13, multiple row lines 14 formed on the glass substrate 13 so as to extend in parallel to each other in a first direction X, and an insulating film 15 that covers the row lines 14. Each of the row lines 14 is formed of, for example, an Al film of 0.1 $\mu$m thickness. For example, 200 row lines 14 are formed on the glass substrate 13 with 50 $\mu$m pitches therebetween. The insulating film 15 may be, for example, a silicon nitride ($Si_3N_4$) film. The row lines 14 are connected to a capacitance detecting circuit 22 that detects an electrostatic capacitance.

The column-line portion 12 includes a flexible film (flexible film substrate) 16, and multiple column lines 17 that are formed on the flexible film 16 so as to extend in parallel to each other in a second direction Y. The flexible film 16 is flexible enough to be deflected along several-micrometer irregularities pressed against the surface of the flexible film 16, and is desirably a polyester film of, for example, about 1 to 30 $\mu$m thickness. Each of the column lines 17 is formed of, for example, an Al film of 0.1 $\mu$m thickness. For example, 200 column lines 17 are formed on the flexible film 16 with 50 $\mu$m pitches therebetween. The column lines 17 are connected to a column selecting circuit 23. The column selecting circuit 23 connects the column lines 17 other than that selected during electrostatic capacitance measurement to a ground.

The spacer 18 is formed along the periphery of the row-line portion 11 and the column-line portion 12, and helps confine an air between the opposing row-line portion 11 and column-line portion 12, thereby forming an air space 19. When an object having small irregularities is pressed against the surface of the flexible film 16, the air confined in the air space 19 causes deflection of the flexible film 16 along the irregularities. An unsealed air space may be formed between the row-line portion 11 and the column-line portion 12. In this case, when the column lines 17 are pressed until they are brought into contact with the insulating film 15, an air is confined between the irregularities, thus achieving a similar function to that of the sealed air space.

The structure of the surface pressure distribution sensor 10 of the present invention, as shown in the equivalent circuit diagram of FIG. 1, allows the capacitance detecting circuit 22 to detect variations of the electrostatic capacitance corresponding to variations in the distance between intersections 21 of the row lines 14 and the column lines 17. The variations of the electrostatic capacitance at the intersections 21, which are caused by the small irregularities pressed against the surface of the flexible film 16, are detected to output signal data indicating the configuration of the irregularities of the object.

Figure 3:
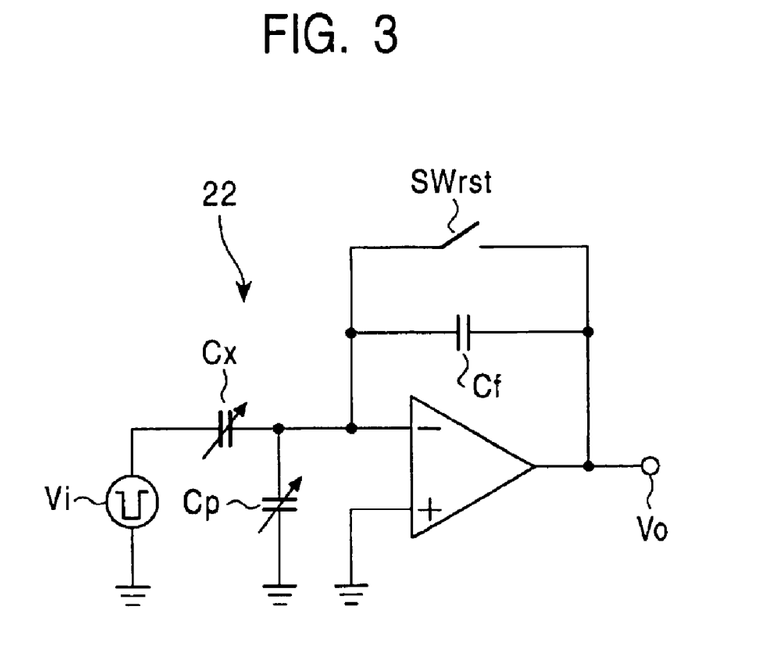
FIG. 3 is an equivalent circuit diagram of a capacitance detecting circuit.

FIG. 3 is an equivalent circuit diagram of the capacitance detecting circuit 22. During measurement, the column lines 17 other than that selected by the column selecting circuit 23 are connected to the ground, and the electrostatic capacitances, not to be measured, on the same row line 14 are input in parallel to a measurement system as parasitic capacitances, which are cancelled since the electrodes at the opposite side of the parasitic capacitances are connected to the ground. This structure allows for high-precision detection of small irregularities, that is, small variations of the electrostatic capacitance.

In this embodiment, the column lines 17 are formed on the flexible film 16. Instead, the row lines 14 may be formed on the flexible film 16. However, in view of low electrostatic susceptibility, the column lines 17 connected to the column selecting circuit 23 with low output impedance are preferably formed on the flexible film 16.

Figure 4:
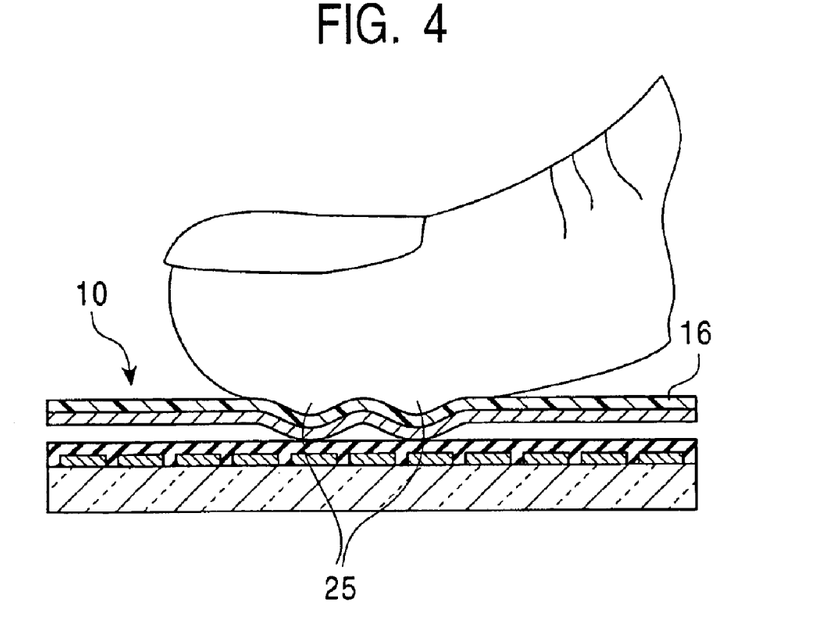
FIG. 4 is a diagram showing irregularity detection of the surface pressure distribution sensor of the present invention.

The surface pressure distribution sensor 10 may be used for any application. The surface pressure distribution sensor 10 may be used as, for example, a fingerprint sensor shown in FIG. 4. When small irregularities 25 of a fingerprint or the like are pressed against the surface of the flexible film 16, the distance between the intersections 21 of the row lines 14 and the column lines 17 varies. Variations of the electrostatic capacitance in response to the variations in the distance are detected to accurately determine the configuration of the small irregularities 25 of the fingerprint or the like and to output signal data indicating the detected configuration.

Figure 5:
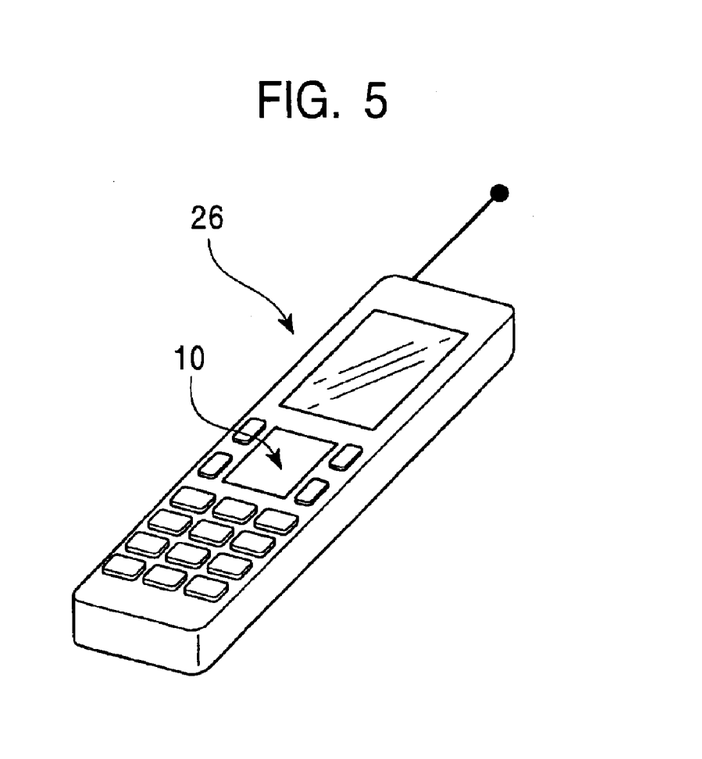
FIG. 5 is an external perspective view of a cellular telephone having the surface pressure distribution sensor of the present invention.

For example, a fingerprint sensor implemented by the surface pressure distribution sensor 10 may be applied to a user authentication system for a cellular telephone 26 shown in FIG. 5. With the recent advancement in payment technologies with the use of potable telephones, such as the cellular telephone 26, the demands for accurate user authentication have increased. The surface pressure distribution sensor 10 mounted on the cellular telephone 26 accurately detects a fingerprint pressed against the surface pressure distribution sensor 10, and verifies the detected fingerprint with fingerprint data registered in advance, thus allowing for accurate authentication of the user of the cellular telephone 26.

Figure 6:
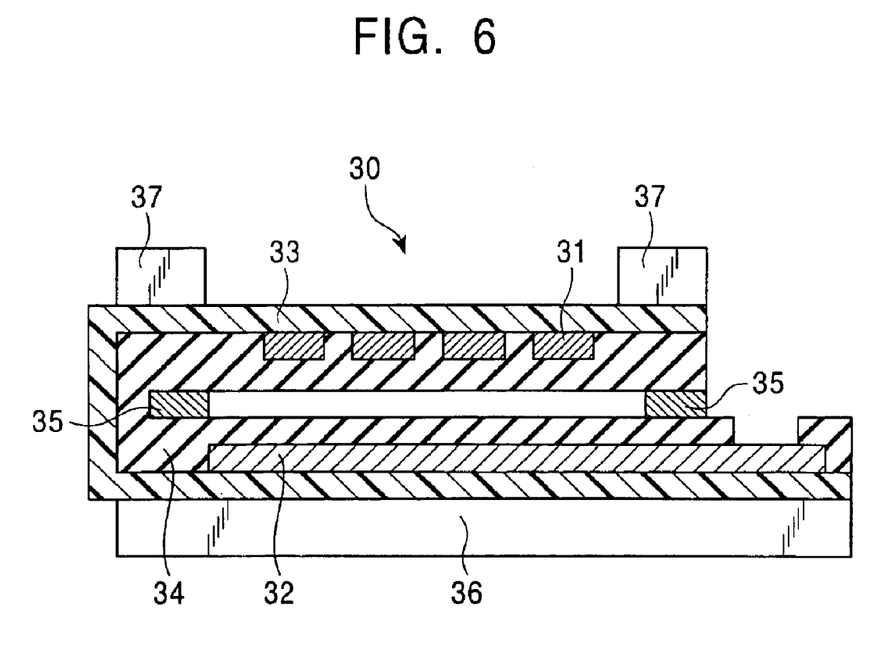
FIG. 6 is an enlarged cross-sectional view of a surface pressure distribution sensor according to a second embodiment of the present invention.
Figure 7A:
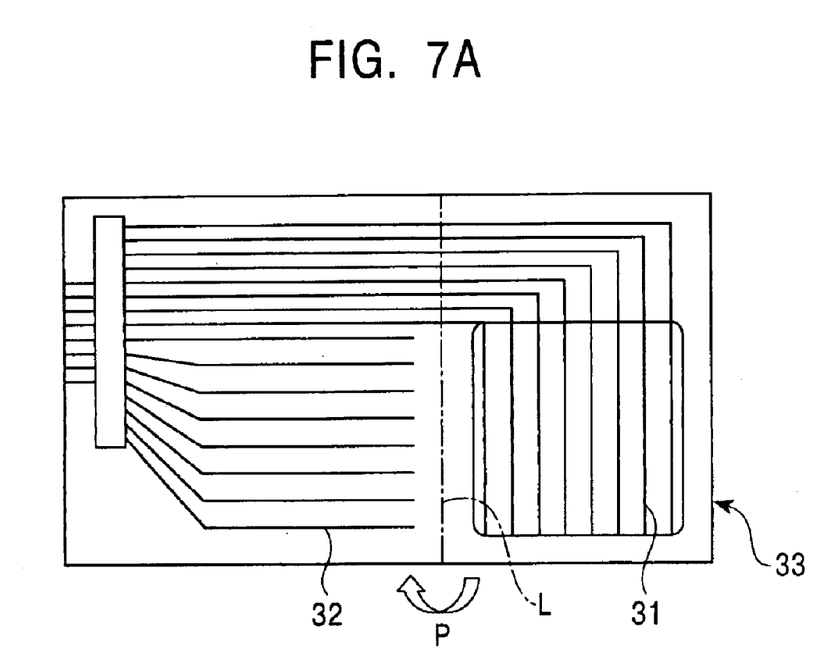
FIGS. 7A and 7B are plan views of a flexible film substrate shown in FIG. 6.
Figure 7B:
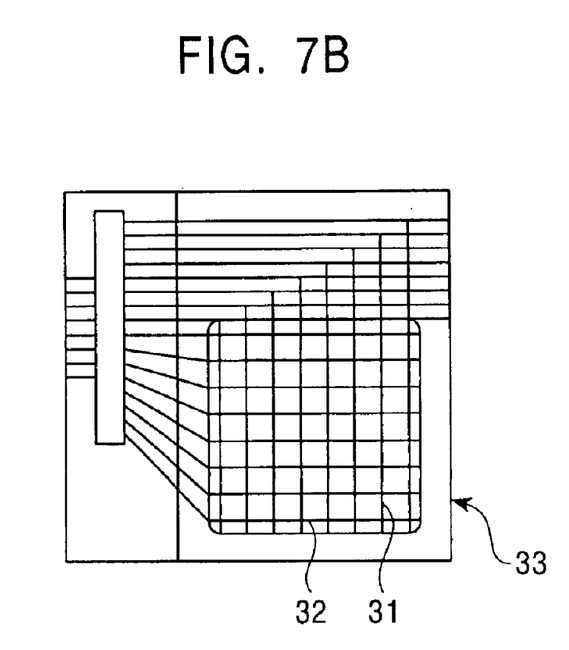

FIG. 6 is an enlarged cross-sectional view of a surface pressure distribution sensor 30 according to a second embodiment of the present invention. In the surface pressure distribution sensor 30 of the second embodiment, column lines 31 and row lines 32 are formed on a single flexible film 33. Referring to FIG. 7A, the column lines 31 and the row lines 32 that extend orthogonal to each other are adjacently formed on the flexible film 33. An insulating film 34 is formed so as to cover the column lines 31 and the row lines 32. The flexible film 33 is folded along a folding line L near the boundary between the column lines 31 and the row lines 32 in the direction indicated by an arrow P so that the column lines 31 and the row lines 32 face each other with the insulating film 34 therebetween (see FIG. 7B).

As shown in FIG. 6, preferably, the flexible film 33 is folded before a spacer 35 is formed for maintaining a certain spacing between the column lines 31 and the row lines 32 that face each other with the insulating film 34 therebetween. The portion of the flexible film 33 that carries the row lines 32 may be adhered to a reinforcing plate 36, for example, a stainless steel (SUS) plate.

A rectangular reinforcing plate 37 may further be formed on the portion of the flexible film 33 that carries the column lines 31 along the periphery of the flexible film 33. For example, when the surface pressure distribution sensor 30 is used as a fingerprint sensor, the reinforcing plate 37 also serves as a partition for guiding the finger to be sensed to the surface pressure distribution sensor 30. The thickness of the reinforcing plates 36 and 37 may be adjusted to provide higher flexibility, thus allowing the surface pressure distribution sensor 30 to be brought into tight contact with a curved area.

Figure 8A:
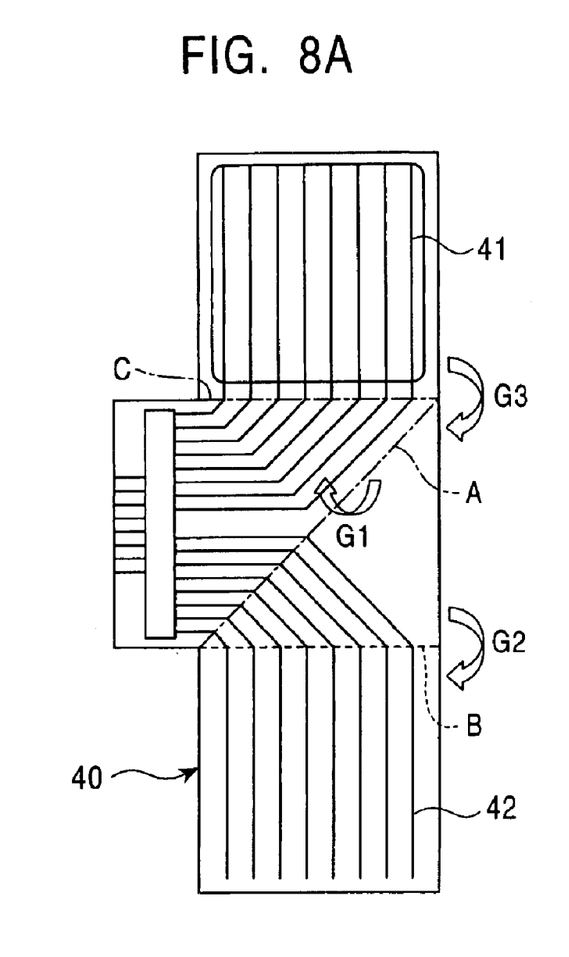
FIGS. 8A and 8B are plan views of a flexible film substrate of a surface pressure distribution sensor according to a third embodiment of the present invention.

For example, as shown in FIG. 8A, column lines 41 and row lines 42 may be formed on a single flexible film 40 so as to extend in the same direction.

First, the flexible film 40 is folded along a diagonal folding line A so that the portion corresponding to the row lines 42 is folded up and to the left, as indicated by an arrow G1.

Figure 8B:
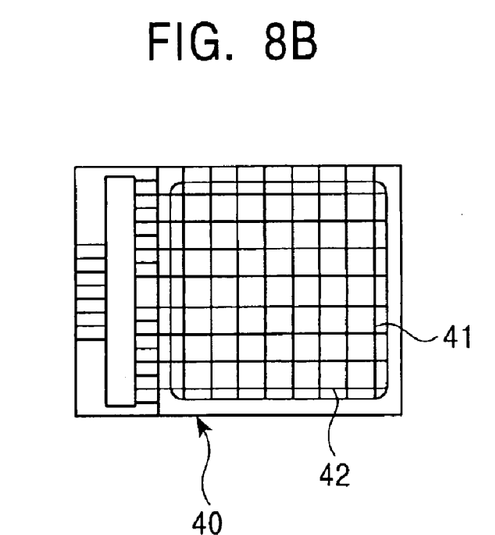

Then, the portion corresponding to the row lines 42 is folded back and to the right, as indicated by an arrow G2, along a folding line B so that the row lines 42 extend horizontally. Then, the portion corresponding to the column lines 41 is folded down, as indicated by an arrow G3, along a folding line C so that the column lines 42 and the row lines 41 orthogonally overlap. Thus, as shown in FIG. 8B, the column lines 41 and the row lines 42 are orthogonal to each other.

The column lines 41 and the row lines 42 formed on the single flexible film 40 so as to extend in the same direction may reach terminals, thus minimizing the unnecessary blank area of the flexible film 40 without wiring on the sensing section.

Figure 9:
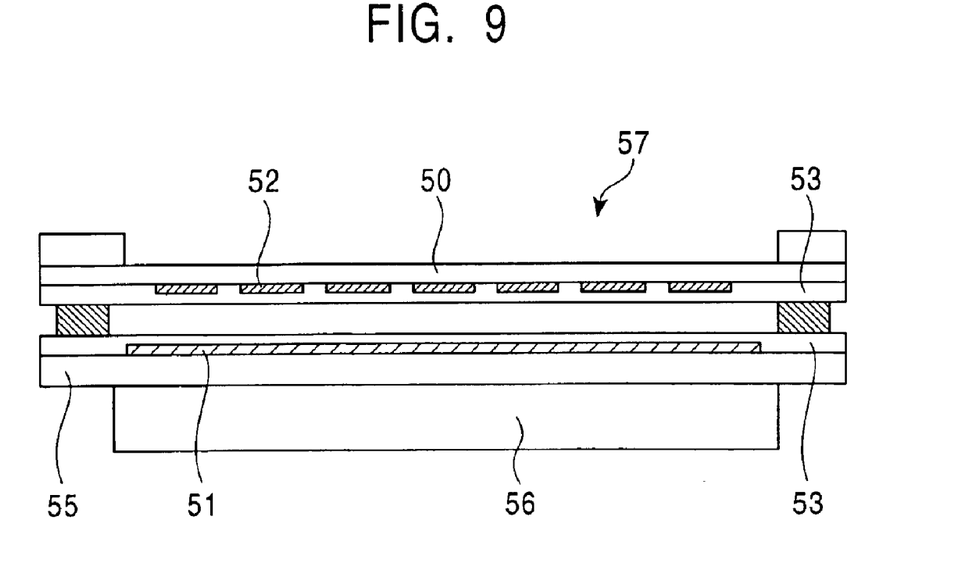
FIG. 9 is a cross-sectional view of a surface pressure distribution sensor incorporated into a display device according to a fourth embodiment of the present invention.

The surface pressure distribution sensor may be incorporated into a display device. As shown in FIG. 9, column lines 52 made of a transparent conductive material, such as ITO (indium tin oxide), are formed on a transparent flexible film 50, and row lines 51 made of a transparent conductive material, such as ITO, are formed on a transparent substrate 55 formed of, for example, a transparent polyester sheet. The transparent row lines 51 and the transparent column lines 52 are coated with transparent insulating films 53. A liquid crystal display 56 or the like is formed so as to underlie the transparent substrate 55. Thus, a display device 57 having a pointing function is realized. The display device 57 may be applied to a display unit of, for example, a cellular telephone, thus realizing a cellular telephone with a pointing function and space-saving design.

Figure 10:
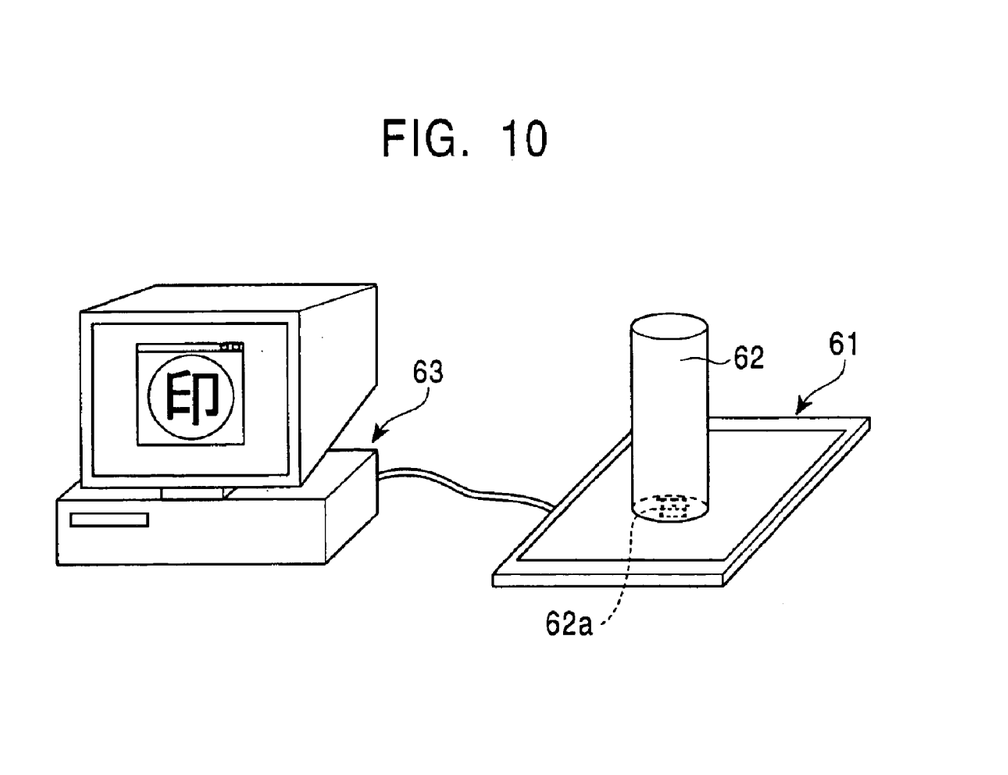
FIG. 10 is a diagram of a surface pressure distribution sensor according to a fifth embodiment of the present invention.

The surface pressure distribution sensor of the present invention may also be used as, for example, a sensor for capturing seal imprints. As shown in FIG. 10, a seal 62 is imprinted on a surface pressure distribution sensor 61 so that irregularities of an imprint 62a of the seal 62 are pressed against the surface pressure distribution sensor 61, and data of the imprint 62a is captured by a personal computer 63 for authentications, seal registration, or the like.

In the foregoing embodiments, the flexible film may be, for example, a polyethylene naphthalate (PEN) film. This flexible film has non-uniform thermal shrinkage across the plane due to the drawing processing in the manufacturing process. An Al thin film or the like formed on the flexible film experiences a tensile stress or a compressive stress depending upon the manufacturing conditions, and such stresses can induce line disconnection. Because of the non-uniformity of the thermal shrinkage across the plane, if the Al thin film or the like experiences a tensile stress, heat treatment after forming the Al thin film or the like on the flexible film causes the row and column lines to extend in the high-thermal-shrinkage direction of the flexible film, thus reducing the occurrence of line disconnection. If the Al thin film or the like formed on the flexible film experiences a compressive stress, the heat treatment causes the row and column lines to extend in the low-thermal-shrinkage direction of the flexible film, thus reducing the occurrence of line disconnection.

What is claimed is:

1. A surface pressure distribution sensor comprising:
  row lines having a plurality of conductors extending in parallel to each other in a first direction;
  column lines having a plurality of conductors extending in parallel to each other in a second direction across the first direction; and
  a substrate including the row lines and a substrate including the column lines,
  wherein at least one of the substrates comprises a flexible film substrate, and a pressure distribution is detected based on an electrostatic capacitance change at intersections of the row lines and the column lines, and
  wherein the substrates are formed of a single flexible film substrate, the row lines and the column lines are formed on the flexible film substrate, and the flexible film substrate is folded at a predetermined position so that the row lines and the column lines intersect with each other.

2. A surface pressure distribution sensor according to claim 1, wherein the row lines and the column lines are formed on first and second independent substrates, respectively, and the first and second substrates overlap so that the row lines and the column lines intersect with each other.

3. A surface pressure distribution sensor of claim 1, wherein the flexible film substrate is made of a resin having different thermal shrinkages in the first and second directions;
  the row lines and the column lines are formed so as to extend in the higher-thermal-shrinkage direction when a film stress caused by the row lines or the column lines is a tensile stress; and
  the row lines and the column lines are formed so as to extend in the lower-thermal-shrinkage direction when the film stress is a compressive stress.

4. A surface pressure distribution sensor of claim 1, at least either the row lines or the column lines are coated with an insulating film.

5. A surface pressure distribution sensor according to claim 4, wherein the flexible film substrate is made of a resin having different thermal shrinkage in the first and the second directions;
  the row lines and the column lines are formed so as to extend in the higher-thermal-shrinkage direction when a film stress caused by the row lines or the column lines and the insulating film is a tensile stress; and
  the row lines and the column lines are formed so as to extend in the lower-thermal-shrinkage direction when the film stress is a compressive stress.

6. A surface pressure distribution sensor according to claim 1, wherein the row lines and the column lines are formed on the flexible film substrate so as to extend in the same direction, and the flexible film substrate is folded so that the row lines and the column lines intersect with each other.

7. A surface pressure distribution sensor comprising:

row lines having a plurality of conductors extending in parallel to each other in a first direction;

column lines having a plurality of conductors extending in parallel to each other in a second direction; and a substrate including the row lines and a substrate including the column lines, wherein at least one of the substrates comprises a flexible film substrate, and a pressure distribution is detected based on an electrostatic capacitance change at intersections of the row lines and the column lines, and wherein the film substrate is made of a resin having different thermal shrinkages in the first and second directions;

the row lines and the column lines are formed so as to extend in the higher-thermal-shrinkage direction when a film stress caused by the row lines or the column lines is a tensile stress; and the row lines and the column lines are formed so as to extend in the lower-thermal-shrinkage direction when the film stress is a compressive stress.

* * * * *